United States Patent
Bartholome

(10) Patent No.: US 6,512,947 B2
(45) Date of Patent: Jan. 28, 2003

(54) HEART RATE MONITORING SYSTEM WITH ILLUMINATED FLOOR MAT

(76) Inventor: David G. Bartholome, P.O. Box 573, Hawley, MN (US) 56549

( * ) Notice: Subject to any disclaimer, the term of this patent is extended or adjusted under 35 U.S.C. 154(b) by 98 days.

(21) Appl. No.: 09/826,536

(22) Filed: Apr. 5, 2001

(65) Prior Publication Data

US 2002/0147410 A1 Oct. 10, 2002

(51) Int. Cl.$^7$ .............................................. A61B 5/024
(52) U.S. Cl. ...................... 600/519; 600/509; 600/520; 482/23
(58) Field of Search ...................... 482/23, 74; 600/509, 600/519, 520; 128/903

(56) References Cited

U.S. PATENT DOCUMENTS

| | | | |
|---|---|---|---|
| 4,434,801 A | | 3/1984 | Jiminez et al. |
| 4,699,378 A | * | 10/1987 | Appelbaum et al. .......... 482/74 |
| 4,830,021 A | | 5/1989 | Thornton |
| 4,867,442 A | | 9/1989 | Matthews |
| 4,911,427 A | | 3/1990 | Matsumoto et al. |
| 5,125,412 A | | 6/1992 | Thornton |
| 5,263,491 A | | 11/1993 | Thornton |
| 5,314,389 A | | 5/1994 | Dotan |
| 5,527,239 A | | 6/1996 | Abbondanza |
| 5,913,727 A | * | 6/1999 | Ahdoot ........................ 463/39 |
| 5,976,083 A | | 11/1999 | Richardson et al. |
| 5,989,157 A | | 11/1999 | Walton |
| 6,077,193 A | | 6/2000 | Buhler et al. |
| 6,336,891 B1 | * | 1/2002 | Fedrigon et al. ............... 482/8 |

\* cited by examiner

Primary Examiner—Carl Layno

(57) ABSTRACT

A heart rate monitoring system for visually indicating to an individual during a workout session the status of their heart rate relative to a desired heart rate. The heart rate monitoring system includes a floor mat having a first light, a second light and a third light within thereof electronically connected to a control unit for controlling the lighting of the lights. A chest unit is attachable to a body of an individual to determine the current heart rate of the user and then transmits via a signal the heart rate data to the control unit.

17 Claims, 6 Drawing Sheets

HEART RATE MONITORING SYSTEM WITH ILLUMINATED FLOOR MAT

BACKGROUND OF THE INVENTION

1. Field of the Invention

The present invention relates generally to heart rate monitoring devices and more specifically it relates to a heart rate monitoring system for visually indicating to an individual during a workout session the status of their heart rate relative to a desired heart rate.

2. Description of the Prior Art

Heart rate monitoring devices have been in use for years. Heart rate monitors are commonly utilized upon exercise machines that indicate the current heart rate of the individual. Various configurations are utilized to detect the heartbeats such as chest straps, hand electrodes and finger receivers. This heart rate is typically expressed within numerical values upon a display screen of the exercise machine.

The main problem with conventional heart rate monitoring devices is that they do not allow an individual during a workout to easily determine whether they are within a desired heart rate range. Another problem with conventional heart rate monitoring devices is that they do not allow a fitness instructor to easily determine the heart rate status of their students during a workout to thereby guide them in their instructions to the students.

Examples of patented heart rate devices which are illustrative of such prior art include U.S. Pat. No. 5,527,239 to Abbondanza; U.S. Pat. No. 5,989,157 to Walton; U.S. Pat. No. 6,077,193 to Buhler et al; U.S. Pat. No. 4,434,801 to Jiminez et al; U.S. Pat. No. 4,830,021 to Thornton; U.S. Pat. No. 4,867,442 to Matthews; U.S. Pat. No. 5,976,083 to Richardson et al; U.S. Pat. No. 5,314,389 to Dotan; U.S. Pat. No. 5,263,491 to Thornton; U.S. Pat. No. 5,125,412 to Thornton; U.S. Pat. No. 4,911,427 to Matsumoto et al.

While these devices may be suitable for the particular purpose to which they address, they are not as suitable for visually indicating to an individual during a workout session the status of their heart rate relative to a desired heart rate. Conventional heart rate devices do not provide an easy to read visual indication of an individual's heart rate much less allowing a fitness instructor to determine their heart rate.

In these respects, the heart rate monitoring system according to the present invention substantially departs from the conventional concepts and designs of the prior art, and in so doing provides an apparatus primarily developed for the purpose of visually indicating to an individual during a workout session the status of their heart rate relative to a desired heart rate.

SUMMARY OF THE INVENTION

In view of the foregoing disadvantages inherent in the known types of heart rate monitoring devices now present in the prior art, the present invention provides a new heart rate monitoring system construction wherein the same can be utilized for visually indicating to an individual during a workout session the status of their heart rate relative to a desired heart rate.

The general purpose of the present invention, which will be described subsequently in greater detail, is to provide a new heart rate monitoring system that has many of the advantages of the heart rate monitoring devices mentioned heretofore and many novel features that result in a new heart rate monitoring system which is not anticipated, rendered obvious, suggested, or even implied by any of the prior art heart rate monitoring devices, either alone or in any combination thereof.

To attain this, the present invention generally comprises a floor mat having a first light, a second light and a third light within thereof electronically connected to a control unit for controlling the lighting of the lights. A chest unit is attachable to a body of an individual to determine the current heart rate of the user and then transmits via a signal the heart rate data to the control unit.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a heart rate monitoring system that will overcome the shortcomings of the prior art devices.

A second object is to provide a heart rate monitoring system for visually indicating to an individual during a workout session the status of their heart rate relative to a desired heart rate.

Another object is to provide a heart rate monitoring system that utilizes a simple to understand lighting system to indicate the current heart rate status of an individual.

An additional object is to provide a heart rate monitoring system that allows a third party such as a fitness instructor to monitor individual student's heart rates.

A further object is to provide a heart rate monitoring system that improves the overall workout experience for an individual.

Another object is to provide a heart rate monitoring system that encourages individuals to workout at their desired aerobic level.

A further object is to provide a heart rate monitoring system that assists in an efficient workout without requiring an individual to terminate their workout to measure their heart rate.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DESCRIPTION OF THE PREFERRED EMBODIMENT

Figure 1:
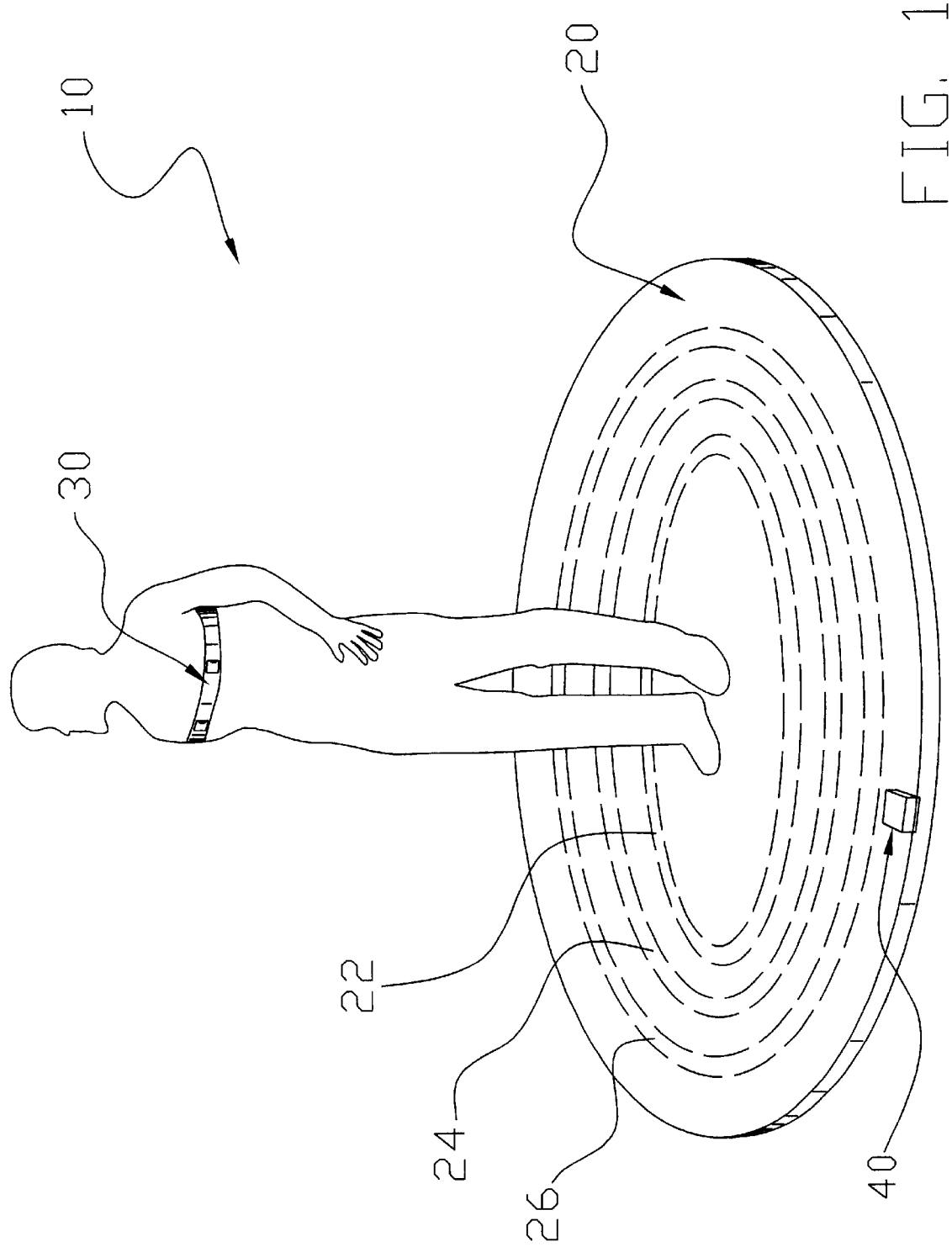
FIG. 1 is an upper perspective view of the present invention with an individual positioned upon the floor mat.

Turning now descriptively to the drawings, in which similar reference characters denote similar elements throughout the several views, FIGS. 1 through 6 illustrate a heart rate monitoring system 10, which comprises a floor mat 20 having a first light 22, a second light 24 and a third light 26 within thereof electronically connected to a control unit 40 for controlling the lighting of the lights 22, 24, 26. A chest unit 30 is attachable to a body of an individual to determine the current heart rate of the user and then transmits via a signal the heart rate data to the control unit 40. It can be appreciated that additional or less lights 22, 24, 26 may be utilized to properly illustrate to the user their current heart rate.

The floor mat 20 is comprised of a relatively broad structure having various shapes and structures. The floor mat 20 may be comprised of a rigid or resilient material as are commonly utilized within the fitness industry. The floor mat 20 is preferably circular in shape however various other shapes may be utilized to construct the floor mat 20.

Figure 3:
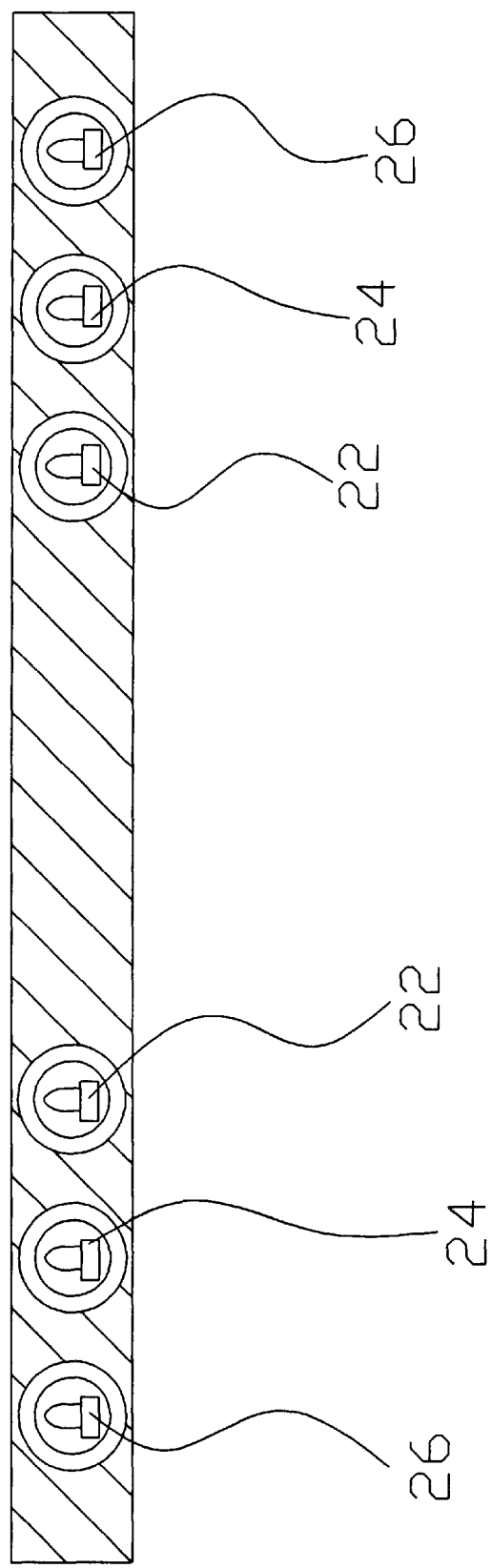
FIG. 3 is a cross sectional view taken along line 3—3 of FIG. 2 illustrating the three light rings.

The floor mat 20 has a height sufficient to support the lights 22, 24, 26 within as illustrated in FIG. 3 of the drawings. The floor mat 20 is also able to support the weight of the individual so as to prevent damage to the lights 22, 24, 26. The floor mat 20 is transparent or semi-transparent directly above each of the lights 22, 24, 26 to allow the light to be emitted from the corresponding lights 22, 24, 26.

Figure 2:
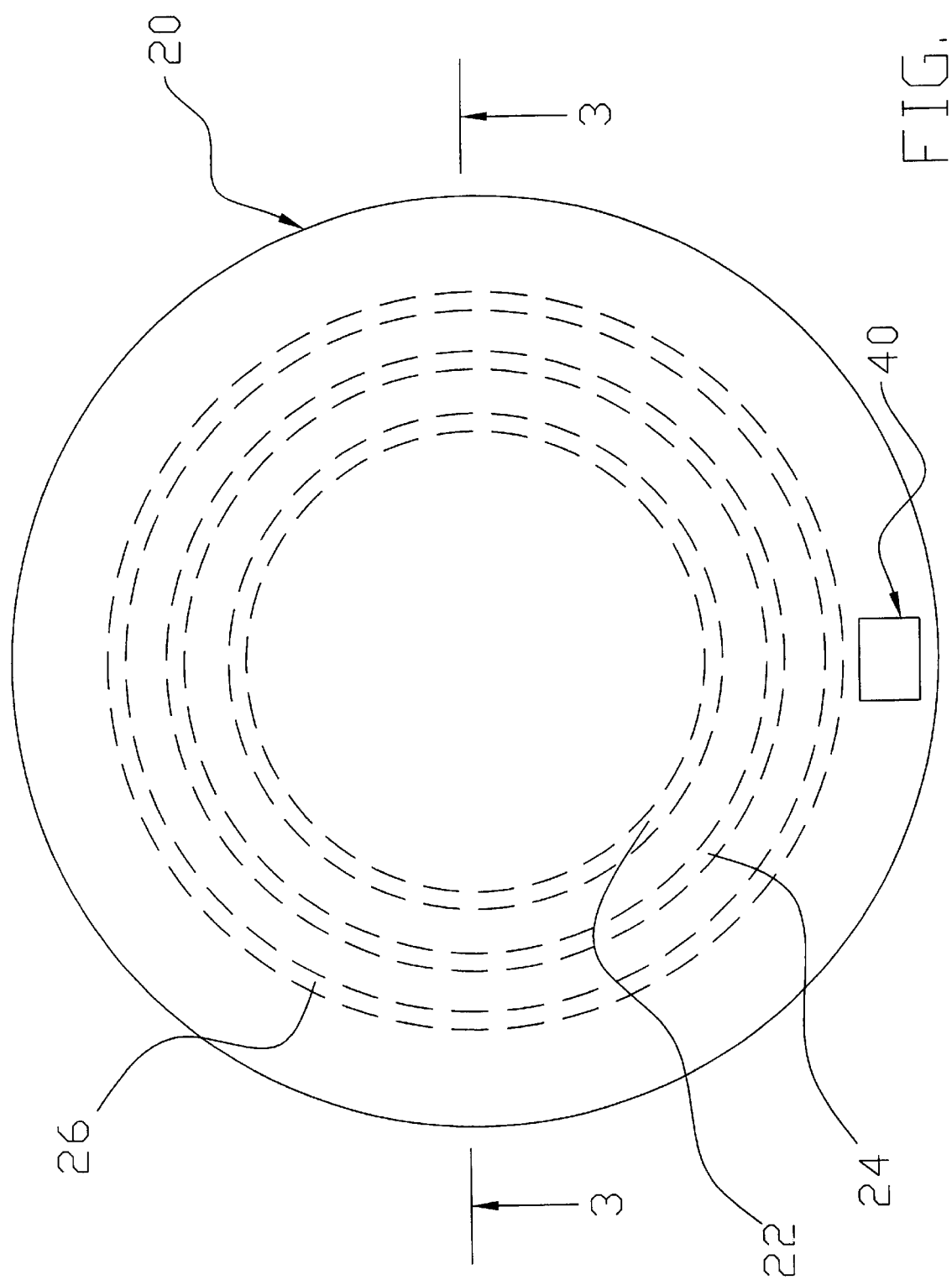
FIG. 2 is a top view of the floor mat.

As shown in FIGS. 1 through 3 of the drawings, a first light 22, a second light 4 and a third light 26 are positioned within the floor mat 20. The lights 22, 24, 26 are preferably positioned concentrically about the floor mat 20 as best illustrated in FIG. 2 of the drawings. The lights 22, 24, 26 may have various other patterns as can be appreciated.

The first light 22 is preferably positioned within the inner portion of the lights 22, 24, 26 as best illustrated in FIGS. 1 through 3 of the drawings. The third light 26 is preferably positioned within the outer portion of the lights 22, 24, 26 as best illustrated in FIGS. 1 through 3 of the drawings. The second light 24 is preferably positioned between the first light 22 and the third light 26 as further shown in the figures. The lights 22, 24, 26 are preferably comprised of a tubular lighting structure that are commonly utilized within various products and lighting devices.

The first light 22 preferably indicates that the heart rate of the user is below the desired or normal range to indicate that the user should increase the intensity of their workout. The first light 22 preferably has a color that indicates a lower than desired heart rate such as blue.

The second light 24 preferably indicates that the heart rate of the user is approximately at the desired or normal range to indicate that the user should maintain the intensity of their workout. The second light 24 preferably has a color that indicates an average or desired rate such as green.

The third light 26 preferably indicates that the heart rate of the user is higher than the desired or normal range to indicate that the user should lower the intensity of their workout. The third light 26 preferably has a color that indicates a higher heart rate such as red.

Figure 5:
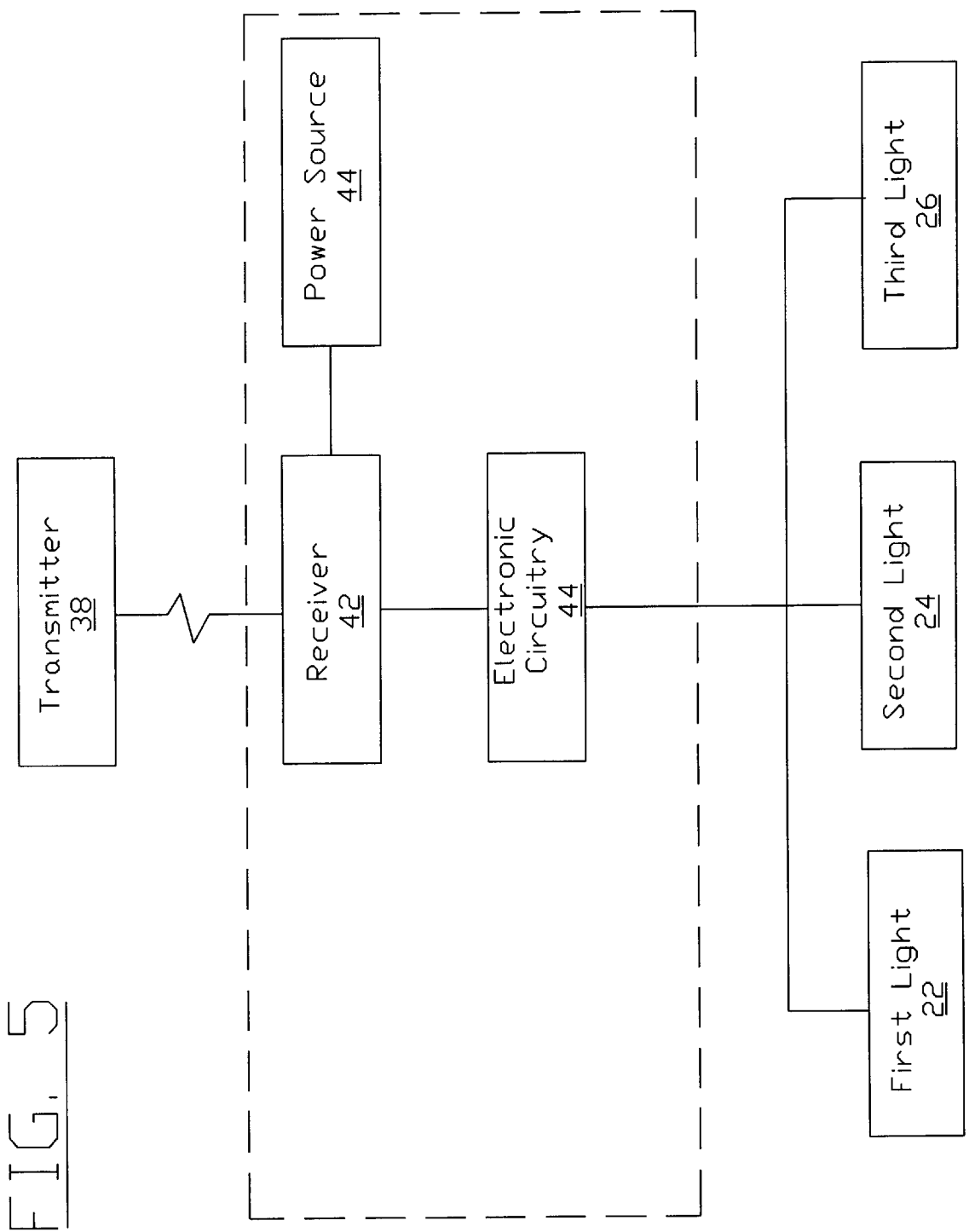
FIG. 5 is a block diagram of the present invention.

As shown in FIGS. 1 and 2 of the drawings, the control unit 40 is secured to the floor mat 20. The control unit 40 is electrically connected to the lights 22, 24, 26 for controlling the illumination of the lights 22, 24, 26 as shown in FIG. 5 of the drawings. The control unit 40 includes a power source 44, electronic circuitry 46 and a receiver 42 for receiving a data signal from the chest unit 30 indicating the current heart rate of the user. Based upon the heart rate data received from the chest unit 30, the control unit 40 controls the illumination of the lights 22, 24, 26 as programmed within the electronic circuitry 46.

Figure 4:
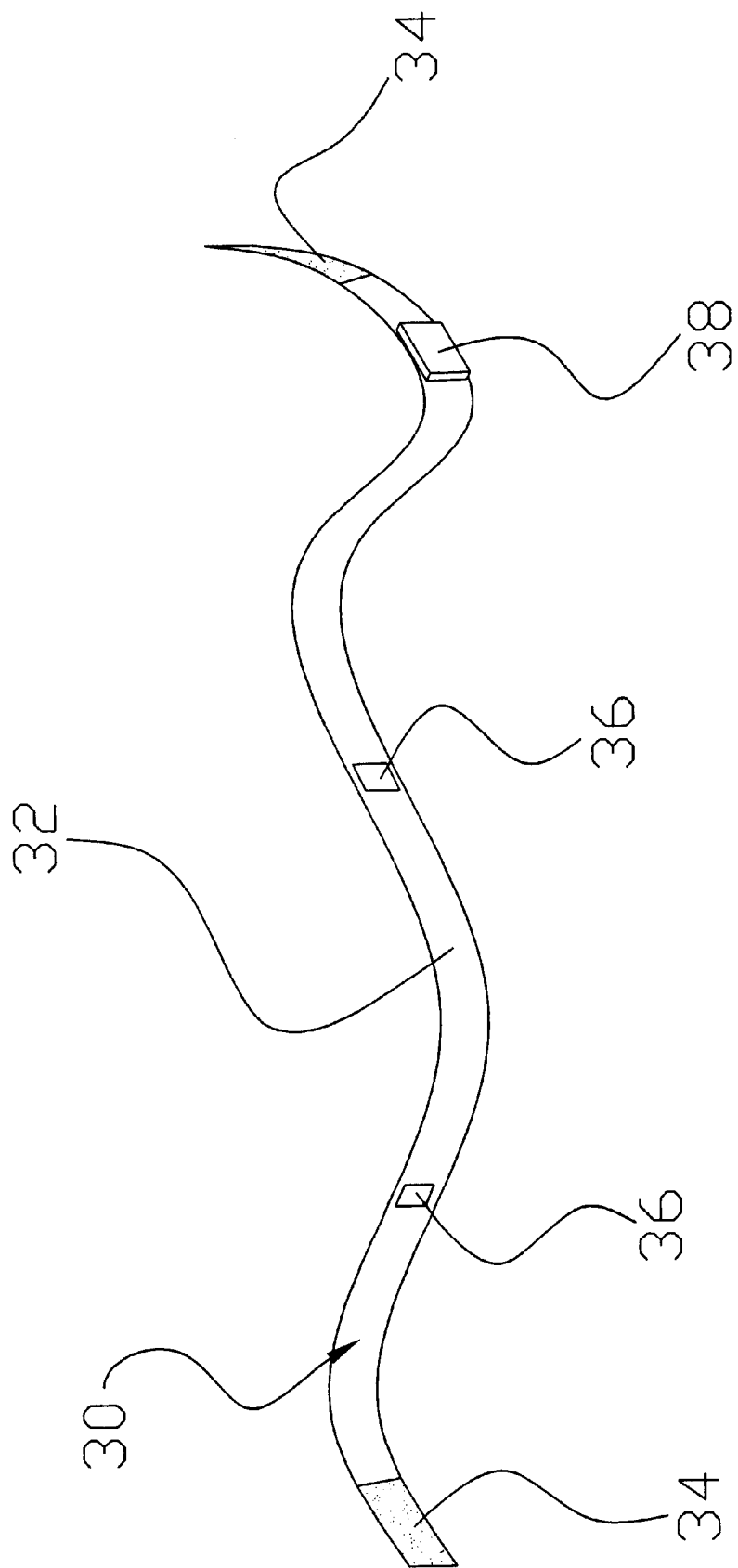
FIG. 4 is an upper perspective view of the chest strap and sensors.

As shown in FIGS. 1 and 4 of the drawings, a chest unit 30 is provided that is attached about the chest of a user to measure the user's current heart rate. The chest unit 30 may be comprised of any well-known heart rate detecting device that detects the heart rate of the user.

The chest unit 30 is preferably comprised of a strap 32 with a securing means 34 such as hook and loop fastener, a plurality of sensors 36 for detecting the heart beats of the user, and a transmitter 38 for transmitting the data signal containing the heart rate information to the control unit 40 which is received by the receiver 42. The chest unit 30 is comprised of conventional electronic circuitry 46 that is well established in the art.

Figure 6:
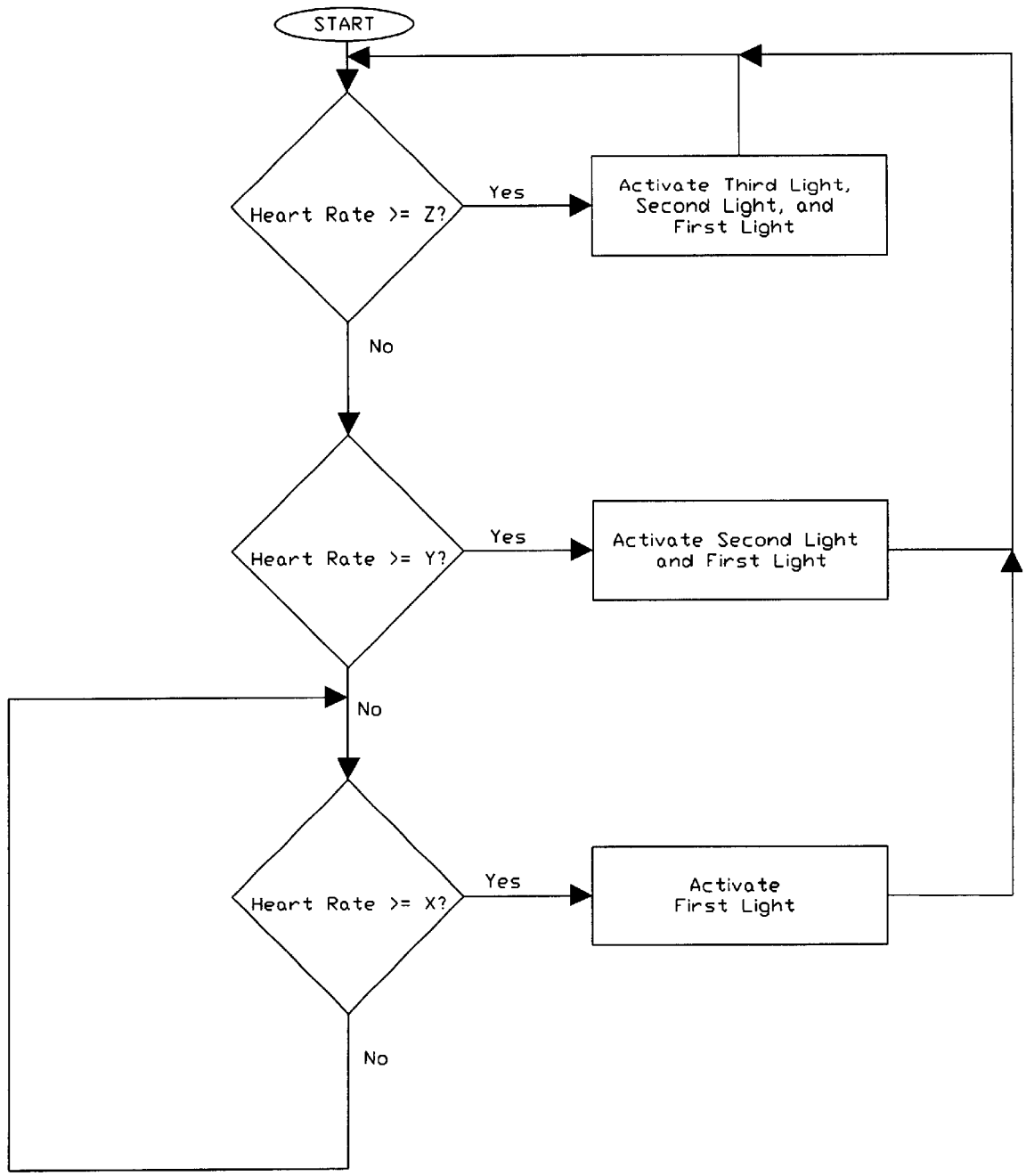
FIG. 6 is a flowchart illustrating one method of controlling the first light, second light and third light dependent upon the heart rate of the user.

In use, the user secures the chest unit 30 about their chest to detect their heart rate. During exercise the chest unit 30 detects the heart rate of the user and transmits the heart rate information to the control unit 40 via a data signal. The control unit 40 receives the heart rate data and determines which of the lights 22, 24, 26 should be activated. FIG. 6 illustrates one method of operating the lights 22, 24, 26 wherein if the heart rate is above a minimum level (X) then the first light 22 is activated, wherein if the heart rate is above a minimum desired level (Y) then the first light 22 and the second light 24 are activated, and wherein if the heart rate is above a maximum desired level (Z) then the first light 22, second light 24 and third light 26 are activated. If the heart rate is below the maximum desired level (Z) then the third light 26 is deactivated, wherein if the heart rate is below the minimum desired level (Y) then the second light 24 is deactivated, and if the heart rate falls below the minimum level (X) then the first light 22 is deactivated. The user visually monitors the lights 22, 24, 26 and adjusts their workout accordingly along with input from the instructor.

In an alternative method of operating the lights 22, 24, 26 not illustrated in the drawings, if the heart rate is above a minimum level (X) then the first light 22 is activated, wherein if the heart rate is above a minimum desired level (Y) then only the second light 24 is activated with the first light 22 deactivated, and wherein if the heart rate is above a maximum desired level (Z) then only the third light 26 are activated with the second light 24 deactivated. If the heart rate is below the maximum desired level (Z) then the third light 26 is deactivated and the second light 24 activated, wherein if the heart rate is below the minimum desired level (Y) then the second light 24 is deactivated and the first light 22 activated, and if the heart rate falls below the minimum level (X) then the first light 22 is deactivated. It can be appreciated that various other features may be utilized with the present invention such as the flashing of the lights 22, 24, 26 when specific events occur.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A heart rate monitoring system, comprising:
   a floor mat;
   a plurality of lights within said floor mat;
   a control unit having a receiver within said floor mat and electrically connected to said plurality of lights; and
   a chest unit having a transmitter for detecting a current heart rate of a user and transmitting said current heart rate to said control unit.

2. The heart rate monitoring system of claim 1, wherein said control unit illuminates said plurality of lights dependent upon said current heart rate.

3. The heart rate monitoring system of claim 2, wherein said floor mat includes a transparent portion above said plurality of lights.

4. The heart rate monitoring system of claim 3, wherein said plurality of lights have different colors indicating various heart rate levels.

5. The heart rate monitoring system of claim 4, wherein said plurality of lights include at least one inner light, at least one central light and at least one outer light.

6. The heart rate monitoring system of claim 5, wherein said inner light indicates a heart rate below a desired level.

7. The heart rate monitoring system of claim 6, wherein said central light indicates a heart rate at said desired level.

8. The heart rate monitoring system of claim 7, wherein said outer light indicates a heart rate above said desired level.

9. The heart rate monitoring system of claim 8, wherein said outer light is activated when said heart rate is above said desired level.

10. The heart rate monitoring system of claim 9, wherein said central light is activated when said heart rate is at said desired level.

11. The heart rate monitoring system of claim 10, wherein said inner light is activated when said heart rate is below said desired level.

12. The heart rate monitoring system of claim 11, wherein said chest unit is comprised of:
    a strap;
    a securing means attached to said strap;
    a plurality of sensors for detecting said current heart rate; and
    a transmitter electrically connected to said plurality of sensors for transmitting said current heart rate to said control unit.

13. The heart rate monitoring system of claim 12, wherein floor mat is circular in shape and wherein said plurality of lights are concentric within said floor mat.

14. A method of operating a heart rate monitoring system having a floor mat, a first light, a second light and a third light within said floor mat with a control unit controlling said lights based upon a current heart rate received from a chest unit, said method comprising the steps of:
    (a) receiving said current heart rate from said chest unit;
    (b) activating said first light if said current heart rate is above a minimal level (X);
    (c) activating said second light if said current heart rate is above a minimal desired level (Y); and
    (d) activating said third light if said current heart rate is above a maximum desired level (Z).

15. The method of operating a heart rate monitoring system of claim 14, including the steps of:
    (e) deactivating said first light if said current heart rate is below a minimal level (X);
    (f) deactivating said second light if said current heart rate is below a minimal desired level (Y); and
    (g) deactivating said third light if said current heart rate is below a maximum desired level (Z).

16. A method of operating a heart rate monitoring system having a floor mat, a first light, a second light and a third light within said floor mat with a control unit controlling said lights based upon a current heart rate received from a chest unit, said method comprising the steps of:
    (a) receiving said current heart rate from said chest unit;
    (b) activating said first light if said current heart rate is above a minimal level (X);
    (c) activating said first light and said second light if said current heart rate is above a minimal desired level (Y); and
    (d) activating said first light, said second light and said third light if said current heart rate is above a maximum desired level (Z).

17. The method of operating a heart rate monitoring system of claim 16, including the steps of:
    (e) deactivating said first light, said second light and said third light if said current heart rate is below a minimal level (X);
    (f) deactivating said second light and said third light if said current heart rate is below a minimal desired level (Y); and
    (g) deactivating said third light if said current heart rate is below a maximum desired level (Z).

* * * * *